(12) United States Patent
Trau (10) Patent No.: US 10,018,554 B2
(45) Date of Patent: Jul. 10, 2018

(54) DISPOSABLE PHOTOMETRIC MEASUREMENT TIP HAVING A CAPILLARY FILLING CHANNEL WITH A CAPILLARY FILLING MECHANISM

(71) Applicant: NATIONAL UNIVERSITY OF SINGAPORE, Singapore (SG)

(72) Inventor: Dieter Wilhelm Trau, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 0 days.

(21) Appl. No.: 15/028,120

(22) PCT Filed: Oct. 9, 2014

(86) PCT No.: PCT/SG2014/000474
§ 371 (c)(1),
(2) Date: Apr. 8, 2016

(87) PCT Pub. No.: WO2015/053713
PCT Pub. Date: Apr. 16, 2015

(65) Prior Publication Data
US 2016/0245739 A1    Aug. 25, 2016

(30) Foreign Application Priority Data
Oct. 11, 2013  (GB) .................................. 1318017.9

(51) Int. Cl.
*G01N 21/03*  (2006.01)
*G01J 3/02*  (2006.01)
(Continued)

(52) U.S. Cl.
CPC ........ *G01N 21/0303* (2013.01); *G01J 3/0291* (2013.01); *G01N 21/8507* (2013.01);
(Continued)

(58) Field of Classification Search
CPC ............... G01N 21/03; G01N 21/0303; G01N 2021/0321; G01N 33/53; G01N 33/5302;
(Continued)

(56) References Cited

U.S. PATENT DOCUMENTS 4,907,037 A * 3/1990 Boisde ............... G01N 21/7703
                                              250/227.28
6,396,584 B1    5/2002 Taguchi et al.
(Continued)

OTHER PUBLICATIONS

International Search report dated Dec. 15, 2014 for PCT/SG2014/000474.

*Primary Examiner* — Que T Le
(74) *Attorney, Agent, or Firm* — Symbus Law Group, LLC; Clifford D. Hyra (57) ABSTRACT

A disposable photometric measurement tip comprising a polymer tip, the polymer tip having a capillary filling channel, the capillary filing channel having an opening at a distal end of the polymer tip, a wave guide channel acting as an optical input coupling and a wave guide channel acting as an optical output coupling, each of the wave guide channels having an opening at a proximal end of the polymer tip wherein the capillary filling channel, the wave guide channel acting as an optical input coupling and the wave guide channel acting as an optical output coupling are connected to each other.

20 Claims, 3 Drawing Sheets

(51) Int. Cl.
*G01N 21/85* (2006.01)
*G01J 1/04* (2006.01)

(52) U.S. Cl.
CPC ........... *G01J 1/0422* (2013.01); *G01J 3/0216* (2013.01); *G01N 2021/0321* (2013.01); *G01N 2021/0346* (2013.01); *G01N 2201/0221* (2013.01); *G01N 2201/08* (2013.01)

(58) Field of Classification Search
CPC ..... G01N 21/8507; B01L 3/02; B01L 3/0275; B01L 3/50271; B01L 3/50273; B01L 3/50275
USPC ..................................... 250/227.11, 239, 573
See application file for complete search history.

(56) References Cited

U.S. PATENT DOCUMENTS

| | | | |
|---|---|---|---|
| 2002/0064800 A1 | 5/2002 | Sando et al. | |
| 2004/0191119 A1 | 9/2004 | Zanzucchi | |
| 2010/0288058 A1* | 11/2010 | Laiho ................... | B01L 3/0275 73/864.01 |
| 2013/0171673 A1 | 7/2013 | Follonier et al. | |

\* cited by examiner

DISPOSABLE PHOTOMETRIC MEASUREMENT TIP HAVING A CAPILLARY FILLING CHANNEL WITH A CAPILLARY FILLING MECHANISM

FIELD OF INVENTION

The current invention relates to a disposable photometric measurement tip for use with a mobile hand held photometer for photometric, luminometric, fluorometric and turbidimetric measurements in liquids.

BACKGROUND OF THE INVENTION

Photometry is an important analytical method with various applications. The current state of the art photometric apparatus is usually a bench top instrument. Photometers can be divided into two groups, instruments using cuvettes and instruments using an immersible sensor. Cuvette based instruments are usually heavy desktop instruments, or smaller portable instruments with reduced functions. Most instruments using immersible sensors are comprised of a desktop unit connected to the immersible sensor via a light guiding glass fiber. The sensor is usually made from metal and or glass. Light originating in the desktop unit is guided through the sensor and passing a defined length of sample volume, then guided back into the desktop unit to a detector. Sensors are bulky and need to be cleaned before transfer into another sample.

Trau and Orban (DE 10149879) describe a handheld photometer using a disposable and immersible sensor tip with a cuvette recess function. In contrast to other instruments, a fraction of the optical path is an integral part of the disposable tip made from polymers. The advantage of this configuration is that sample contamination and sample cross contamination can be totally ruled out by exchanging a new tip for each measurement. The tip of DE 10149879 however has the disadvantage of a long optical path length the light has to travel through the tip material, resulting in low transmission. A characteristic feature of the tip of DE 10149879 is that the tip is partly immersed into the measurement solution and all parts of the hand held photometer are above the meniscus of the measurement solution. The liquid to be analyzed is then flowing into the optical recess of the tip which is acting as a cuvette. The tip of DE 10149879 also needs a reflective surface such as a metallic surface adding complexity and cost. The current invention overcomes several limitations by providing a photometric measurement tip using different types of light propagation.

SUMMARY OF THE INVENTION

The current invention describes a novel measurement principle and design based on light propagation to perform photometric, luminometric, fluorometric, nephleometric and turbidimetric measurements in particular in combination with hand-held photometers. The tip of the current invention does not use a recess as cuvette as described by Trau and Orban. Instead an inner channel within the tip is filled with the liquid to be analyzed and the channel is acting as a waveguide or light propagation channel to guide light through the liquid sample for absorbance and other optical measurements. Most advantageously the tip can be made as a disposable to prevent any cross contamination and-re-quires only minute amounts of sample volumes. Advantageously, the channel acting as a waveguide can be dimensioned to only guide light of one wavelength to become a monochromator. By using a tip of the current invention, no monochromator is necessary in the photometric device leading to a drastic cost reduction of the photometric device.

According to a first aspect of the invention there is provided a disposable photometric measurement tip comprising a polymer tip, the polymer tip having a capillary filling channel, the capillary filing channel having an opening at a distal end of the polymer tip, a wave guide channel acting as an optical input coupling and a wave guide channel acting as an optical output coupling, each of the wave guide channels having an opening at a proximal end of the polymer tip wherein the capillary filling channel, the wave guide channel acting as an optical input coupling and the wave guide channel acting as an optical output coupling are connected to each other.

The polymer tip may have has a length between 0.5 and 10 centimeter.

The polymer tip may have a diameter between 50 micrometer to 10 milimeter at its capillary filling channel end.

The polymer tip may have a has a diameter between 1 millimeter and 20 milimeter at its optical coupling end.

The polymer tip may be formed of a polymer material having a refractive index lower than 1.33.

The polymer tip may have a film or coating with low refractive index applied onto the inner wall of the waveguide channel acting as a cladding.

The polymer tip may have a microstructured surface forming a two-dimensional periodic array or structure of air holes or air filled regions which is applied onto the inner wall of the waveguide channel and exhibiting a photonic bandgap effect and acting as a cladding.

The capillary channel and the waveguide channel may have a cross section between 1 micrometer square and 1 milimeter square.

The cross section of the capillary filling channel and the wave guide channel may be different.

At least one of the cross section of the capillary filling channel and the cross section of the wave guide channel may change over the channel length.

The wave guide channel may have a meander or folded shape such that the length of the wave guide channel is a multiple of the tip length.

The multiple may be less than 1000.

The capillary filling channel and the wave guide channel may be the same.

The opening of the wave guide channel acting as the optical input coupling and the opening of the wave guide channel acting as the optical output coupling may be the same.

The dimensions and bending angles of the wave guide channel may be selected to only guide light of a particular wave length interval.

The dimensions and bending angles of the wave guide channel may be selected to only guide light of one wavelength.

The dimensions and bending angles of the wave guide channel may be selected to only guide light above a particular refractive index.

The tip may have more than one waveguide channel.

At least one prism and or at least one reflective surface may be used to guide the light.

The capillary filling channel may have an integrated filter.

The disposable photometric measurement tip may have one wave guide channel acting as an optical input coupling connected to more than one wave guide channel acting as an optical output coupling.

The disposable photometric measurement tip may have one wave guide channel acting as an optical output coupling connected to more than one wave guide channel acting as an optical input coupling.

The tip may contain a reagent which is mixed with the sample filling up the channels.

The tip may comprise a reservoir cavity containing at least one reagent and the reservoir cavity may be connected to at least one channel.

According to a second aspect of the invention there is provided a system for performing photometric measurements, the system comprising a disposable photometric tip according to the first aspect of the invention, a light source connected to the wave guide channel acting as an optical input coupling and a light detector connected to the wave guide channel acting as an optical output coupling.

The system may be operable to perform photometric or fluorometric or turbidimetric or nephleometric or refractive index measurements.

According to a third aspect of the invention there is provided a method of performing photometric measurements using a system according to the second aspect of the invention, the method comprising the steps of supplying light from the light source to the wave guide channel acting as an optical input coupling, immersing the distal end of the tip into a liquid sample such that liquid is drawn into the capillary filling channel and the waveguide channel, and detecting transmitted light at the light detector.

Definitions

Figure 1:
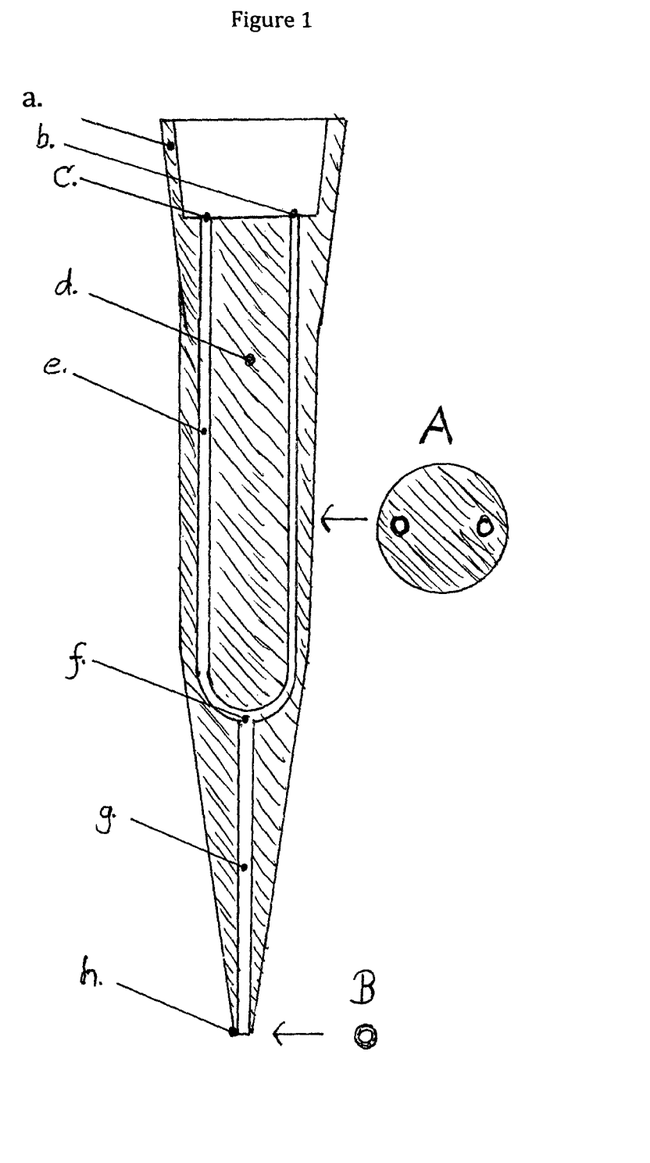
Figure 2:
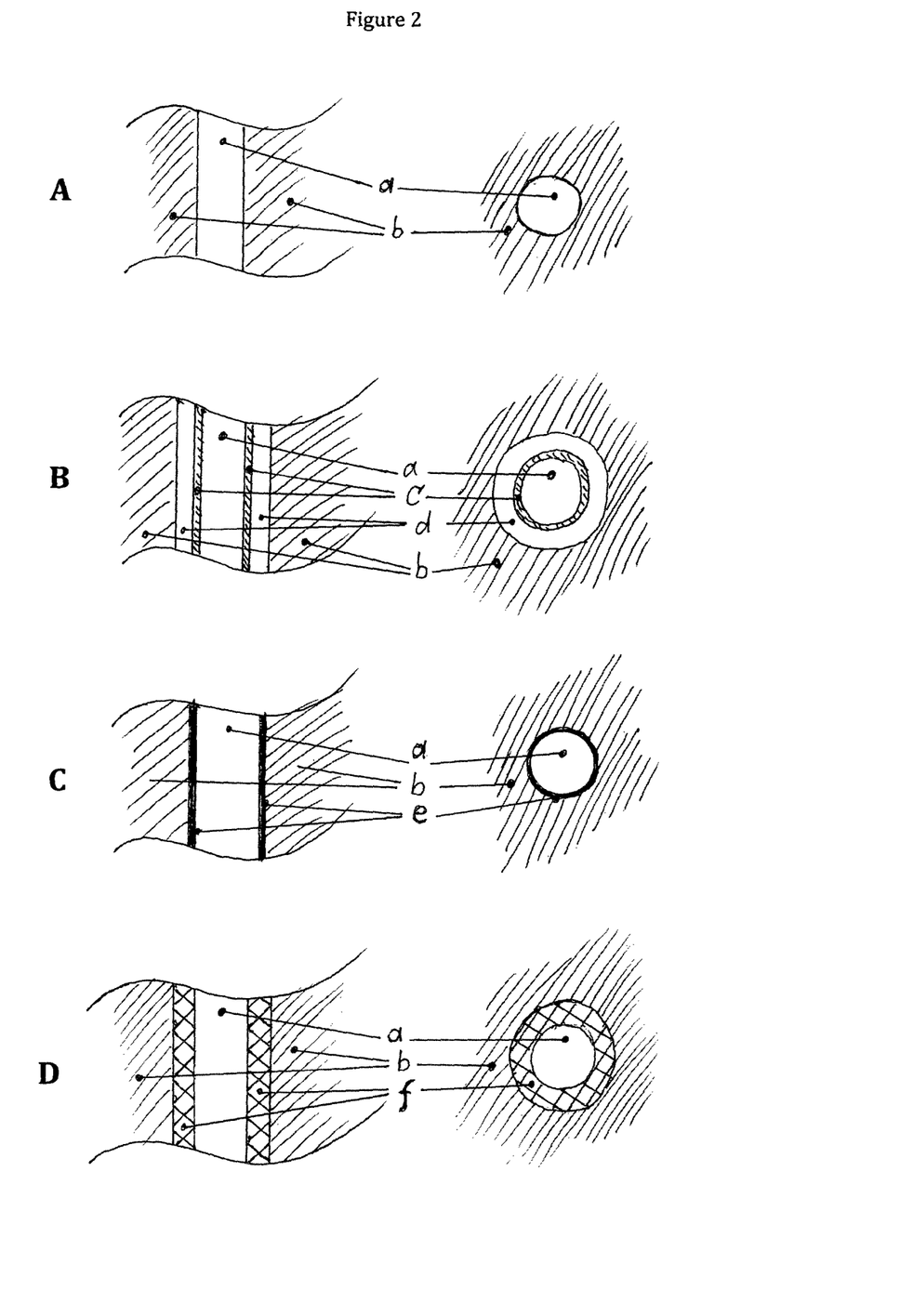
Figure 3:
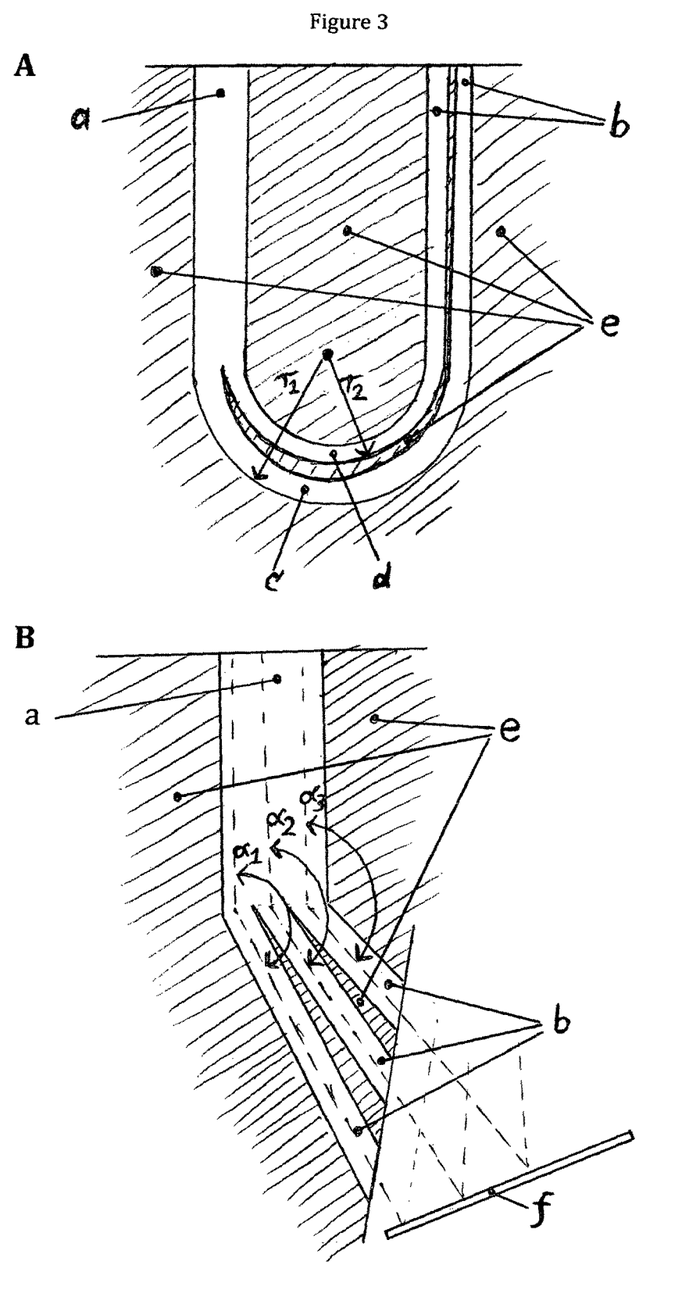

The term "disposable" or "disposable tip" or "photometric measurement tip" or "tip" means the tip of the current invention. The tip is made from a polymer or glass. Typically the tip has on one distal end the opening of a capillary filling channel and on its opposite distal end the opening of a wave guide channel acting as optical input coupling and a second opening of the same waveguide channel acting as the optical output coupling. The capillary filling channel and the wave guide channel are connected to each other. The tip has a length between 0.5 and 10 centimeter. The tip may have a diameter between 50 micrometer and 2 cm; the diameter on the two distal ends may be different. Typically the capillary filling channel distal end has a much smaller diameter or cross section compared with the opposite distal end connected to the photometric device. The channels have a diameter of 1 micrometer to 500 micrometer; the cross section can be round, rectangular or of any other shape. An example of a tip of the current invention is given in FIG. 1.

The term "waveguide channel" means a channel within the tip which is filled with the sample. The sample can be a liquid or a gas. Due to the refractive index of the tip material and the sample and the channel dimensions light can propagate through the waveguide channel. Light propagation can be achieved by total internal reflection or by the use of reflective surfaces on the waveguide channel such as a reflective metallic surface or by microstructured coatings or films with a refractive index considerable lower that of water wherein light propagates by total internal reflection or is confined by the bandgap effect or mixtures thereof. The waveguide can be designed as a multimode waveguide or a single-mode waveguide to guide multiple wavelengths or only a single wavelength of light. Light guided through the waveguide may be from the ultraviolet (UV) region to the infrared region (IR).

The term "capillary filling channel" means a channel within the tip which is filled with the sample. The sample is flowing through the capillary filling channel by capillary action into the waveguide channel to fill the waveguide channel by capillary action with sample. The capillary filling channel may contain means to condition the sample such as a filter or a reagent release container.

The term "capillary filling" means to fill the capillary channel and the waveguide channel with a sample by the use of capillary force or capillary action.

The term "optical coupling" means the process and the technical feature on the tip to couple light from a photometer device or a light source into the waveguide channel and couple light out of the waveguide channel into a photometric device. The tip has at least one waveguide channel ending at one distal end of the tip. The ending of the waveguide channel is termed "optical coupling".

The term "optical input coupling" and "optical output coupling" means the two ends of the waveguide channel to couple light into the waveguide and couple light out of the waveguide. Light coupled out of the waveguide is typically transmitted onto a light sensor.

The term "measurement" means the process of using the tip and the attached photometric device to analyze and determine the concentration of an analyte in the sample.

The term "hand held photometric device" means a mobile device containing at least one light source and at least one light detector connected to the tip of the current invention to perform photometric measurements.

The term "analyte" means the species to be analyzed by performing a measurement, typically a chemical compound such as but not limited to proteins, peptides, nucleic acids, lipids, dextran, gases, metabolites such as but not limited to glucose, billirubine or a biological compound such as but not limited to microorganism, virus, cells or a biomarker or a pH value or tubidimetry or nephleometry or a color or a mixtures thereof.

The term "bending angle" means the bend of the waveguide channel to create a curved waveguide channel. The bending angle must be large enough not to lose too much light. By using bending of the waveguide channel a longer channel can be integrated into a small tip. This type of meander or folded shape of the channel can create a channel length of up to 1000 times longer than the tip length.

The term "cuvette" means a transparent container to hold a sample for a photometric/spectrometric measurement. Classical cuvettes are made from glass or polymers. In Trau and Orban the cuvette is an optical recess filled with the sample. In the present invention the cuvette is the waveguide channel filled with the sample.

DETAILED DESCRIPTION OF THE INVENTION

In the following disclosures examples are provided for the better understanding of the current invention and should not be interpreted to limit the current invention. The current invention relates to a photometric measurement tip which is using a channel filled with the sample to be analyzed as a waveguide. This waveguide channel is acting as a cuvette. Advantageously light is guided through the sample by using total internal reflection. If total internal reflection is used as the wave propagation principle, the tip material's refractive index must be lower than the samples refractive index. For aqueous liquid samples the tip materials refractive index should be bellow the refractive index of water of 1.33.

However, most polymer materials have a refractive index larger than water. To solve this problem several inventive solutions are disclosed in the present invention. Instead using a tip material with low refractive index a thin film with low refractive index can be applied or coated onto the inner wall of the waveguide channel. Such film can have an refractive index close to or bellow 1 (The journal of Polymers for Advanced Technologies 03/2003; 4(1):1-7. DOI: 10.1002/pat.1993.220040101). The low refractive index film or coating can have a thickness in the nanometer up to micrometer the regime.

Several types of coatings or films could be applied for this purpose such as film that contain a large amount of air such as super hydrophobic films or porous films. Air has a refractive index of close to one and will reduce the total refractive index of the film or coating. In this embodiment the inner surface of the waveguide channel is coated with an air cladding structure (Kaiser P. V., Astle H. W., 1974, Bell Syst. Tech. J., 53, 1021-1039). Another air cladding structure can be achieved by the deposition of micrometer size air balons (A. Fery et al.) The air cladding can be also achieved by building a thin air gap around the waveguide channel. The air gap thickness can be from several nanometers to micrometers. The air gap structure can be build by injection molding of a polymer or by other molding processes. The liquid sample is confined in a thin polymer tube. The polymer tube is surrounded by an air gap and the entire structure is within the polymer tip. Light, will be refracted from the liquid sample core into the polymer tube and then totally internal reflected on the polymer tube interface to the air gap. The light enters again the liquid core by refraction. The polymer of the tube should have a refractive index close to the liquid sample to avoid total internal reflection on the tube liquid interface.

In another embodiment of the present invention hollow core photonic bandgap fibers or photonic crystal fibers or Bragg fibers are used to guide the light through the tip. In this embodiment the waveguide channel is formed by a Photonic bandgap fiber, photonic crystal fiber or a Bragg fiber. The Bragg fiber is a photonic-bandgap fiber formed by concentric rings of multilayer film. The fiber structure is formed by microstructuring the inner surface of the waveguide channel of the tip to create the photonic bandgap effect for light propagation. This microstructured inner surface is acting as the cladding of the fiber and the hollow channel filled with sample is the core. In general the cladding exhibits a two-dimensional periodic array or structure of air holes or air filled regions. Photonic bandgap fibers, photonic crystal fibers and Bragg fibers including the disclosed hollow tip with a microstructured inner surface which is an analogue of such fibers do not rely on total internal reflection instead light is guided and confined by the band gap effect and by hollow air filled microstructures.

For the disclosed light guiding means most advantageously, light can be guided to turns or meanders without the use of metal reflective surfaces or prisms. However reflective surfaces or prisms could be used alternatively. A turn in the waveguide channel geometry will cause light to have different angles of incident at the inner and outer turn radius. To guide all light rays by total internal reflection the turning radius should be as large as possible and or the difference in the refractive index between the tip material and the sample should be as large as possible. If those conditions are not properly controlled the light intensity at the output end will be reduced and may interfere with adsorption measurements. Inventively, this behavior of the current invention can be used to construct a tip to measure the refractive index of a sample, as it will be disclosed later. The liquid sample filled channel is acting as a waveguide. The waveguide channel can be dimensioned to only guide light of one wavelength (single-mode waveguide) to become a monochromator. By using a tip of the current invention, no monochromator is necessary in the photometric device leading to a drastic cost reduction of the photometric device. The current invention moves the monochromator from the device into the tip. By changing different tips a different wavelength can be used for photometric measurements. It is also possible to integrate more than one single-mode waveguide channel into the tip for multi wavelength measurements.

By using the wave propagation mechanism of total internal reflection or the bandgap effect or light confinement by microstructured surfaces containing a large volume of air regions the disposable tip of the current invention does not need metallic reflective surfaces or optical components such as lenses or prisms and therefore can be manufactured at a very low price.

The disposable photometric measurement tip of the current invention is composed of:
i) A polymer tip,
ii) Having on one distal end the opening of a capillary filling channel,
iii) Having an the other distal end the opening of a wave guide channel acting as optical input coupling and the opening of a wave guide channel acting as the optical output coupling,
iv) And in which the capillary filling channel and the wave guide channel acting as optical input coupling and the wave guide channel acting as the optical output coupling are connected to each other.

The optical input coupling can be connected to a light source and the optical output coupling can be connected to a light detector. The light source and the light detector are part of a photometric device; preferentially the photometric device is a hand held photometer. By immersing the tip into a liquid sample the capillary filling channel and the waveguide channel are filled with the sample. Light from the light source is coupled into the tip and exits at the optical output coupling from the tip and is projected onto a light detector. The absorbance of the sample can now be measured to analyze the sample. The optical path length is given by the length of the waveguide channel. Because the light is propagating by total internal reflection, the geometrical length of the waveguide channel may be different from the optical path length. This difference is corrected by a correction factor. The correction factor can be determined by a calibration with a substance of known concentration and absorbance coefficient using the Lambert Beer Law. Tips of the same design can then be used with the corresponding correction factor.

Typically with absorbance measurements a large number of different analytes can be quantitatively measured. For example absorbance measurements at 260 nm are used to measure proteins, absorbance measurements at 280 nm are used to measure nucleic acids such as DNA, RNA and oligonucleotides.

Absorbance measurements at around 600-700 nm are used to measure particle concentrations. In this case light is scattered and only some light is absorbed. The scattered light does not reach the detector and is a measure for the particle concentration.

In another embodiment of the current invention the waveguide channel is a single-mode waveguide allowing only light of a defined wavelengths to propagate.

This can be achieved by the channel dimensions and the refractive indexes of the tip material. Advantageously this allows the use of only a single light source emitting a brought spectrum of white light. The wavelength that is used, for example for absorbance measurement, is determined by the light propagation property of the waveguide which is integrated into the tip. All existing photometric devices contain a monochromator as part of the device. The monochromator can be a filter, a grid or a prism or is realized by using a monochromatic light source such as a laser or a LED with a defined wavelength. The novel feature of the present invention is that the function of the monochromator is integrated into the tip acting as a "cuvette".

As a person skilled in the art will immediately realize, that using the waveguide channels of the tip as monochromators will allow building a spectrometer or photometer device for a very low prize solving a major problem of current spectrometer/photometer instruments. Different wavelength may be selected by using different tips. More than one single-mode waveguide can be integrated into the tip to perform multi wavelength measurements. By fully utilizing the novel concept of the current invention spectrometer/photometer devices may become generally available for a large user group and may become a commodity.

In another embodiment of the current invention the tip has one optical input coupling of a waveguide channel connected to more than one waveguide channels ending with an optical output coupling. Advantageously the optical input coupling channel is a multimode channel and the more than one optical output coupling channels are different single-mode channels or vice versa.

In another embodiment of the current invention the capillary filling channel has an integrated filter to prevent particles entering the waveguide channel.

In another embodiment of the current invention the waveguide channel is coated with a reflective surface, typically but not limited to a metallic reflective surface to achieve light propagation through the waveguide channel by reflection on the metallic channel surface.

In another embodiment of the current invention the tip has a conical shape at its optical coupling end to attach, the tip to a photometric device. The conical shape may also adjust the optical coupling positions of the tip with the optical coupling positions of the photometric device. Other shapes than conical may be used to achieve the alignment; such other shapes may use a notch or mechanical features to achieve alignment and attachment.

If more than one single-mode waveguide channel is integrated into the tip the wavelength to be measure is addressed by: A) Having a separate light source for every channel and switching on the light source to address a particular channel. B) Having a separate light detector for every channel and reading out the corresponding light detector to address a particular channel. C) By having a capillary filling mechanism that fills all waveguide channels sequentially in time and obtaining sequential measurements in time to address the particular channel.

Advantageously, the tip and photometric system of the current invention can be used with a minimal sample volume. With channels in the micrometer regime the required sample volume is less than 1 microliter. One of the novel features of the tip is the capillary filling channel. By dipping into a sample the entire tip channels such as the capillary filling channel and the waveguide channel are filled with sample by capillary filling. To fill the channels a small drop of sample can be used. The tip and system can be used during the operation of a patient to fill the tip with blood or other body fluids for measurements such as oxygen, glucose or biomarkers.

In another embodiment of the current invention the tip is used for turbidimetric or nephleometric measurements in liquids. Any dispersed colloidal system will scatter light and a certain fraction of this scattered light will not longer propagate through the waveguide channel by total internal reflection or by reflection on metallic surfaces and will not reach the end of the optical output coupling. Using this principle a sample with colloidal particles or cells will reduce the light intensity measured with the detector.

In another embodiment of the current invention the tip is used for refractive index measurements of a liquid sample. A tip of the current invention to measure refractive index has a straight waveguide channel geometry followed by a turned waveguide channel geometry. A turn in the waveguide channel geometry will cause light to have different angles of incident at the inner and outer turn radius. If the turn radius is reduced the angle of incident is becoming smaller. At a certain value of incident light the conditions for total internal reflection or the bandgap effect are no longer fulfilled and light is refracted into the tip media and lost. This condition is reached faster for samples with low refractive index. In other words, samples with high refractive index are able to propagate through waveguide turns of a smaller turning radius. Apart from the refractive index and the turning radius, light propagation is a function of the wavelength. The standard wavelength used for refractive index measurements is the sodium D-line of 589 nm. Herein several designs to construct a refractive index measurement tip of the current invention are disclosed.

In a first design, the tip contains a straight waveguide channel geometry followed by only one turned waveguide channel geometry. A monochromatic light source is used. This design is of limited dynamic range.

In a second design, the tip contains a straight waveguide channel geometry followed by only one turned waveguide channel geometry. A polychromatic light source is used. This design has a larger dynamic range but requires a spectrometer to analyse the result.

In a third design, the tip contains a straight waveguide channel geometry followed by at least two turned waveguide channel geometries of different turning radius. A monochromatic light source is used. This design has a larger range of incident light angles resulting in larger dynamic range.

Another design to construct a refractive index measurement tip is using a discrete change of the waveguide channel and not a turn. In this embodiment a linear part of the waveguide channel follows another linear part wherein the two waveguide channels meet at a discrete angle. The angle can be from 0 degree to 90 degree. At a fixed angle say 2 degree light of a certain refractive index is totally internal reflected and light of a slightly lower refractive index is not total internal reflected. In an advanced design a large number of such angles are incorporated into the design. For example, 20 different units of the design are integrated within the measurement tip (any number of units between 2 and 1000 can be used). Each unit has a different angle. After filling all units with the sample a number of such units will transmit the light by total internal reflection. Above a certain critical angle light will not be transmitted by the units. By measuring the light intensity of all 20 units the unit with the critical angle can be identified. By knowing the refractive index of the material of the unit the refractive index of the sample can be calculated. Alternatively instead to measure the light intensity of each unit, the total light intensity of the 20 units can be measured. The design can be also build by using the disclosed microstructured coatings or films acting as a cladding. To reduce the error of refractive index measurements a larger number of units can be used. A reflective surface or prism can be used after the total internal reflection unit to guide the light back to the light detector.

In another embodiment of the current invention the tip has a coating or shielding to prevent ambient light to be coupled into the waveguide channel. The coating or shielding can be applied onto the outer surface of the tip or at the inner surface of the waveguide channel or within the tip material.

In another embodiment of the current invention the tip channel contains a reagent which is mixed with the sample at the time the tip is used and the channel is filled up with sample. The tip may contain a reservoir cavity containing the reagent in where the reservoir cavity is connected to at least one channel. The reagent may undergo a reaction with an analyte in the sample. Typically a color is formed during the reaction to perform colorimetric or photometric analysis of the analyte. In this embodiment the filling channel may contain a mixing region to mix the reagent with the sample before entering the waveguide channel. The reagent can be a dye, a fluorophore, an enzyme, an antibody, a chelating reagent, a metal indicator, a pH indicator, an oxidant, an reducing agent, a buffer, an adsorbent or ion exchanger to remove a chemical species from the liquid sample or mixtures thereof. Alternatively the reagent cam be also premixed with the liquid sample. An example of this embodiment is the use of a pH sensitive dye or fluorophores as a reagent. While filling the channel with sample the pH sensitive dye will exhibit a color or fluorescence as a function of the pH value of the sample. By measuring the color/fluorescence or the ratio of more than one color/fluorescence values to each other the pH value of the sample can be determined. Examples for pH sensitive dyes are phenolphthalein, fluorescein, 7-Hydroxycoumarin-3-carboxylic acid, rhodamine, m-cresol purple, 4-(9-diethylamino-5H-7-oxa-4b,6,13-triaza-indeno [2,1-a]anthracen-5-yl)-2-methoxy-6-nitro-phenol (ACIB) and their derivatives.

In another embodiment of the current invention the channels within the tip may contain a flow restrictor and/or a capillary pump to control the flow speed of capillary filling. The flow restrictor is used to control the flow speed or to stop the flow. The capillary pump is used to create larger capillary pressure to fill channels or cavities of the tip.

Optionally the tip can be used after the measurement to store the sample for future analysis. This is possible because the thin channel will not allow the sample to evaporate.

The tip of the current invention solves several problems which are associated with photometry and overcomes several current limitations, for example: 1) The tip requires no metallic reflective surfaces or optical components such as lenses or prisms to guide the light and therefore can be manufactured at a very low cost. 2) For the first time the expensive monochromator is realized within a disposable tip and the wavelength is selected by selecting different tips reducing the cost of the entire photometric apparatus drastically. 3) Cross contamination between samples is impossible. 4) Extremely small sample volumes can be measured. 5) The sample can be sucked into the tip from a droplet or another source and the tip is removed from the sample source for measurement. 6) The tip can be used to store a sample aliquot after the measurement for future analysis. 7) The tip can be made very small and thin to access all type of reaction tubes found in laboratories or other sample sources. 8) Small amounts of polymeric tip material are necessary reducing the cost of the tip. 9) Tips can be used to measure different analytes and parameters including refractive index. 10) A reaction with a reagent incorporated into the tip can be performed to analyze various chemical species to realize a Lab-in-a-Tip. 11) The tip and photometric device can be hand held for lab bench or environmental measurements.

DETAILED DESCRIPTION OF THE DRAWINGS

Drawings are provided for the better understanding of the current invention and should not be interpreted to limit the current invention. For better illustration the drawing dimensions may not be to scale.

FIG. 1: Depicts a tip of the current invention. Having on one distal end the opening of a capillary filling channel (h) and having an the other distal end the opening of a wave guide channel acting as optical input coupling (b) and the opening of a wave guide channel acting as the optical output coupling (c) and in which the capillary filling channel (g) and the wave guide channel acting as optical input coupling and the wave guide channel acting as the optical output coupling are connected to each other at one point (f). The capillary filling channel is ending at the opposite distal end (h) of the tip. The tip body (d) is typically made from a polymer or glass. The tip may have a conical ending (a) to connect the tip to a photometric device. The cross section (A) depicts the tip body with the waveguide channel. The cross section (B) depicts the opening of the capillary filling channel. The depicted tip is the simplest variation and should not be interpreted to limit the current invention. The filling and waveguide channels may have different shapes such as bends or are folded to achieve a longer length. The diameter of the channels may very over the length of the channels. The tip body may be round or oval or rectangular or of any other shape. The point at which the capillary filling channel is connected to the waveguide channel may be at any point on the waveguide channel. More than one capillary filling channel and waveguide, channel may be integrated into the tip.

FIG. 2: Depicts details and the cross section of tip designs of the current invention. A) Tip design and cross section using a polymeric material with a refractive index below 1.33 depicting the waveguide channel (a) and the tip material (b). B) Tip design and cross section using an air gap, depicting the waveguide channel (a), the tip material (b), the air gap (d) and the tube structure (c) holding the liquid sample within the waveguide channel (a). C) Tip design and cross section of a waveguide channel with an inner reflective coating depicting the waveguide channel (a), the tip material (b) and the reflective coating material (e). D) Tip design and cross section using a microstructured layer, coating of film on the inner waveguide channel, depicting the waveguide channel (a) acting as core, the tip material (b), and the microstructured coating or cladding (f). Typically the coating acts as a cladding exhibiting a bandgap effect to confine light within the inner hollow core filled with the liquid sample. Typically the cladding contains an array or regular or non-regular structures filled with air.

FIG. 3: Depicts designs of a tip of the current invention to measure refractive index. A) Tip design based on curved waveguide channels (c) and (d) with different turning radius r1 and r2, depicting the waveguide channel input coupling (a) and the waveguide channel output coupling (b), the tip material (e). B) Tip design based on at two waveguide channels starting at (a) and ending at (b) and wherein the two waveguide channels meet at a discrete angle ($\alpha 1$). The figure depicts 3 units of such assemblies with different angles ($\alpha 1$) and ($\alpha 2$) and ($\alpha 3$). A sample of a certain refractive index may only guide light by total internal reflection up to a critical angle. In the example Figure light may be guided by the units with the angle (α1) and (α2) but not by the unit with the angle (α3). By measuring the light intensity at the point (b) the light guiding unit with the critical angle can be identified and the refractive index of the sample can be calculated. Optionally a reflective surface or prism (f) is used to guide light back to the detector. For better illustration only 3 different units are depicted; the tip may contain up to 1000 of such units to provide accurate refractive measurements. For both designs A and B a capillary channel is connected to the waveguide channel at any position to fill the waveguide channel with sample. The inner surface of the waveguide channel can have a coating acting as a cladding and exhibiting a bandgap effect to confine light within the inner hollow core filled with the liquid sample. Typically the cladding contains an array or regular or non-regular structures filled with air.

Embodiments of the invention will be summarized in the following paragraphs.

Paragraph 1, A disposable photometric measurement tip composed of:
  v) A polymer tip,
  vi) Having on one distal end the opening of a capillary filling channel,
  vii) Having an the other distal end the opening of a wave guide channel acting as optical input coupling and the opening of a wave guide channel acting as the optical output coupling,
  viii) And in which the capillary filling channel and the wave guide channel acting as optical input coupling and the wave guide channel acting as the optical output coupling are connected to each other.

The tip of Paragraph 1 wherein, a light source is connected to the optical input coupling and a light detector is connected to the optical output coupling to perform photometric or fluorometric or turbidimetric or nephleometric or refractive index measurements.

The tip of Paragraph 1 wherein, the tip has a length between 0.5 and 10 centimeter.

The tip of Paragraph 1 wherein, the tip has a diameter between 50 micrometer to 10 milimeter at its capillary filling channel end.

The tip of Paragraph 1 wherein, the tip has a diameter between 1 millimeter and 20 milimeter at its optical coupling end.

The tip of Paragraph 1 wherein, the polymer material has a refractive index lower than 1.33.

The tip of Paragraph 1 wherein, the tip has a film or coating with low refractive index applied onto the inner wall of the waveguide channel acting as a cladding.

The tip of Paragraph 1 wherein, the tip has a microstructured surface forming a two-dimensional periodic array or structure of air holes or air filled regions which is applied onto the inner wall of the waveguide channel and exhibiting a photonic bandgap effect and acting as a cladding.

The tip of Paragraph 1 wherein, the capillary channel and the waveguide channel have a cross section between 1 micrometer square and 1 milimeter square.

The tip of Paragraph 1 wherein, the cross section of the capillary channel and the waveguide channel is different and changes over the channel length.

The tip of Paragraph 1 wherein, the wave guide channel has a meander or folded shape of a multiple of the tip length at which the multiple is a number of up to 1000.

The tip of Paragraph 1 wherein, the capillary channel and the wave guide channel are the same.

The tip of Paragraph 1 wherein, the opening of the optical input coupling and the opening of the optical output coupling are the same.

The tip of Paragraph 1 wherein, the dimensions and bending angles of the wave guide channel are selected to only guide light of a particular wave length interval or only guide light of one wavelength.

The tip of Paragraph 1 wherein, the dimensions and bending angles of the wave guide channel are selected to only guide light above a particular refractive index.

The tip of Paragraph 1 wherein, the tip has more than one waveguide channel.

The tip of Paragraph 1 wherein, at least one prism and or at least one reflective surface is used to guide the light.

The tip of Paragraph 1 wherein, the capillary filling channel has an integrated filter.

The tip of Paragraph 1 wherein, the tip has one optical input-coupling channel connected to more than one optical output coupling channels or vice versa.

The tip of Paragraph 1 wherein, the tip contains a reagent which is mixed with the sample filling up the channels.

The tip of Paragraph 1 wherein, the tip contain a reservoir cavity containing at least one reagent and in where the reservoir cavity is connected to at least one channel.

A system and method to perform photometric measurements by using:
  i) A polymeric disposable photometric measurement tip,
  ii) Having on one distal end the opening of a capillary filling channel,
  iii) Having an the other distal end the opening of a wave guide channel acting as optical input coupling and the opening of a wave guide channel acting as the optical output coupling,
  iv) And in which the capillary filling channel and the wave guide channel acting as optical input coupling and the wave guide channel acting as the optical output coupling are connected to each other.
  v) And in which the optical input coupling is connected to a light source and the optical output coupling is connected to a light detector
  vi) And in which immersion of the tip into a liquid sample at its distal end of the capillary filling channel causes the filling of the channels with sample to perform a photometric or fluorometric or turbidimetric or nephleometric or refractive index measurement.

The invention claimed is:

1. A disposable photometric measurement tip comprising;
a polymer tip, the polymer tip having;
a capillary filling channel to receive a liquid sample, the capillary filing channel having an opening at a distal end of the polymer tip, the distal end of the capillary filling channel having a diameter in the range 1 μ to 500 μm to provide a capillary filling mechanism,
a wave guide channel to receive the liquid sample through the connected capillary filling channel, wherein the waveguide channel has two openings at the other end of the tip and the two openings are connected to guide light through the liquid sample from one opening to the other opening,
wherein one opening of the wave guide channels acts as an optical input coupling for light to pass into the liquid sample and one opening of the wave guide channel acts as an optical output coupling for light from the liquid sample, and
wherein the capillary filling channel, the wave guide channel acting as an optical input coupling and the wave guide channel acting as an optical output coupling are connected to each other.

2. A disposable photometric measurement tip according to claim 1 wherein the polymer tip has a length between 0.5 and 10 centimeter and a diameter between 1 millimeter and 20 millimeters at its optical coupling end.

3. A disposable photometric measurement tip according to claim 1 wherein the polymer tip is formed from a polymer material having a refractive index lower than 1.33.

4. A disposable photometric measurement tip according to claim 1 wherein the polymer tip has a film or coating with low refractive index applied onto the inner wall of the waveguide channel acting as a cladding.

5. A disposable photometric measurement tip according to claim 1 wherein the polymer tip has a microstructured surface forming a two-dimensional periodic array or structure of air holes or air filled regions which is applied onto the inner wall of the waveguide channel and exhibiting a photonic bandgap effect and acting as a cladding.

6. A disposable photometric measurement tip according to claim 1 wherein the capillary channel and the waveguide channel have a cross section between 1 micrometer square and 1 millimeter square.

7. A disposable photometric measurement tip according to claim 1 wherein at least one of:
the cross section of the capillary filling channel and the wave guide channel is different; and
at least one of the cross section of the capillary filling channel and the cross section of the wave guide channel changes over the channel length.

8. A disposable photometric measurement tip according to claim 1 wherein the wave guide channel has a meander or folded shape such that the length of the wave guide channel is a multiple of the tip length.

9. A disposable waveguide according to claim 8 wherein the multiple is less than 1000.

10. A disposable photometric measurement tip according to claim 1 wherein the capillary filling channel and the wave guide channel are the same.

11. A disposable photometric measurement tip according to claim 1 wherein the opening of the wave guide channel acting as the optical input coupling and the opening of the wave guide channel acting as the optical output coupling are the same.

12. A disposable photometric measurement tip according to claim 1 wherein the dimensions and bending angles of the wave guide channel are selected from one of:
only guide light of a particular wave length interval; and
only guide light of one wavelength.

13. A disposable photometric measurement tip according to claim 1 wherein the dimensions and bending angles of the waveguide channel are selected to only guide light above a particular refractive index.

14. A disposable photometric measurement tip according to claim 1 comprising at least one of the following:
the tip has more than one waveguide channel;
at least one prism and/or at least one reflective surface is used to guide the light; and
the capillary filling channel has an integrated filter.

15. A disposable photometric measurement tip according to claim 1 having one wave guide channel acting as an optical input coupling connected to more than one wave guide channel acting as an optical output coupling.

16. A disposable photometric measurement tip according to claim 1 having one wave guide channel acting as an optical output coupling connected to more than one wave guide channel acting as an optical input coupling.

17. A disposable photometric measurement tip according to claim 1 wherein the tip containing the liquid sample includes a reagent mixed with the sample for filling up the capillary filling channels in the tip.

18. A disposable photometric measurement tip according to claim 17 wherein the tip comprises a reservoir cavity containing at least one reagent and wherein the reservoir cavity is connected to at least one channel.

19. A system for performing photometric measurements, the system comprising;
a disposable photometric tip comprising
a polymer tip, the polymer tip having;
a capillary filling channel to receive a liquid sample, the capillary filling channel having an opening at a distal end of the polymer tip, the distal end of the capillary filling channel having a diameter in the range 1 µto 500 µm to provide a capillary filling mechanism,
a wave guide channel to receive the liquid sample through the connected capillary filling channel, wherein the wavequide channel has two openings at the other end of the tip and the two openings are connected to guide light through the liquid sample from one opening to the other opening,
wherein one opening of the wave guide channels acts as an optical input coupling for light to pass into the liquid sample and one opening of the wave guide channel acts as an optical output coupling for light from the liquid sample, and
wherein the capillary filling channel, the wave guide channel acting as an optical input coupling and the wave guide channel acting as an optical output coupling are connected to each other,
a light source connected to the wave guide channel acting as an optical input coupling and
a light detector connected to the wave guide channel acting as an optical output coupling.

20. A method of performing photometric measurements, the method comprising the steps of:
providing a system for performing photometric measurements, the system comprising;
a disposable photometric tip comprising;
a polymer tip, the polymer tip having;
a capillary filling channel, the capillary filing channel having an opening at a distal end of the polymer tip,
a wave guide channel acting as an optical input coupling and a wave guide channel acting as an optical output coupling, each of the wave guide channels having an opening at a proximal end of the polymer tip
wherein the capillary filling channel, the wave guide channel acting as an optical input coupling and the wave guide channel acting as an optical output coupling are connected to each other, a light source connected to the wave guide channel acting as an optical input coupling and
a light detector connected to the wave guide channel acting as an optical output coupling,
the method comprising supplying light from the light source to the wave guide channel acting as an optical input coupling,
immersing the distal end of the tip into a liquid sample such that liquid is drawn into the capillary filling channel and the waveguide channel, and
detecting transmitted light at the light detector.

* * * * *